(12) United States Patent
Müller et al.

(10) Patent No.: US 9,901,419 B2
(45) Date of Patent: Feb. 27, 2018

(54) SYRINGE

(71) Applicant: Ivoclar Vivadent AG, Schaan (LI)

(72) Inventors: Frank Müller, Feldkirch (AT); Lutz Vocke, Rohrschach (CH)

(73) Assignee: Ivoclar Vivadent AG, Schaan (LI)

( * ) Notice: Subject to any disclaimer, the term of this patent is extended or adjusted under 35 U.S.C. 154(b) by 190 days.

(21) Appl. No.: 14/647,913

(22) PCT Filed: Apr. 9, 2014

(86) PCT No.: PCT/EP2014/057167
§ 371 (c)(1),
(2) Date: May 28, 2015

(87) PCT Pub. No.: WO2014/167004
PCT Pub. Date: Oct. 16, 2014

(65) Prior Publication Data
US 2015/0335397 A1    Nov. 26, 2015

(30) Foreign Application Priority Data

Apr. 9, 2013   (DE) .................. 10 2013 103 552

(51) Int. Cl.
*A61C 5/04*   (2006.01)
*A61C 5/68*   (2017.01)
(Continued)

(52) U.S. Cl.
CPC .................. *A61C 5/68* (2017.02); *A61C 5/64* (2017.02); *A61C 9/0026* (2013.01); *A61M 5/19* (2013.01);
(Continued)

(58) Field of Classification Search
CPC ........... A61C 5/60–5/68; A61C 9/002–9/0026; A61C 19/06–19/066; A61C 19/08;
(Continued)

(56) References Cited

U.S. PATENT DOCUMENTS 2,381,955 A    8/1945   Hoffman et al.
3,166,221 A *  1/1965   Nielsen .................. A61M 3/00
                                                        222/137

(Continued)

FOREIGN PATENT DOCUMENTS

CH            669164 A5    2/1989

*Primary Examiner* — Stephen R Crow
*Assistant Examiner* — Garrett Atkinson
(74) *Attorney, Agent, or Firm* — Ann M. Knab; Thad McMurray (57) ABSTRACT

The invention relates to a syringe, in particular for dispensing flowable dental materials, comprising a syringe housing, at least two storage chambers (12 and 14) for dental materials, which lie transversely adjacent to each other as viewed in the dispensing direction, and a mixing device (36), which has two mixing channels (54, 56, 58, and 60), wherein each mixing channel is connected to the outlet of a storage chamber (12 and 14). The mixing device (36) has a mixing zone (80), which is connected to a pre-mixing zone (64). The pre-mixing zone (64) has two inlets, one for each of the dental materials to be mixed, and an outlet, wherein the inlets point toward each other. The outlet of the pre-mixing zone (64) extends perpendicularly to the inlets. The inlet of the mixing zone (80) is connected to the outlet of the pre-mixing zone (64). The mixing zone (80) has an impact element for deflecting the pre-mixed flow of the dental materials to an outlet of the mixing zone (80).

21 Claims, 6 Drawing Sheets (51) Int. Cl.
*A61M 5/24* (2006.01)
*A61C 9/00* (2006.01)
*A61M 5/19* (2006.01)
*A61C 5/64* (2017.01)
B05C 17/005 (2006.01)
B65D 81/32 (2006.01)

(52) U.S. Cl.
CPC ... *A61M 5/2448* (2013.01); *A61M 2202/0007* (2013.01); *A61M 2210/0625* (2013.01); *B05C 17/00553* (2013.01); *B05C 17/00593* (2013.01); *B65D 81/325* (2013.01)

(58) Field of Classification Search
CPC ........ A61M 5/2448; A61M 5/00–5/19; A61M 2210/0625; A61M 2202/0007; B05C 17/00593; B05C 17/00553; B65D 81/325
USPC ................ 433/80–90; 604/500–522
See application file for complete search history.

(56) References Cited

U.S. PATENT DOCUMENTS

| | | | | |
|---|---|---|---|---|
| 3,894,338 A * | 7/1975 | Loge | ........................ | A61C 1/18 433/82 |
| 3,952,920 A * | 4/1976 | Bergman | ................ | B27G 11/00 222/137 |
| 4,117,551 A * | 9/1978 | Brooks | ................. | B05B 7/1209 222/148 |
| 4,538,920 A * | 9/1985 | Drake | ................... | B01F 5/0615 222/137 |
| 4,600,403 A * | 7/1986 | Wagner | ................. | A61M 5/425 604/115 |
| 4,623,337 A * | 11/1986 | Maurice | ................ | A61F 9/0008 222/390 |
| 4,968,299 A * | 11/1990 | Ahlstrand | ........... | A61M 5/2448 604/191 |
| 5,116,315 A * | 5/1992 | Capozzi | ........... | A61B 17/00491 222/137 |
| 5,535,922 A * | 7/1996 | Maziarz | ................. | B05C 17/01 222/137 |
| 6,048,201 A * | 4/2000 | Zwingenberger | .... | A61C 9/0026 222/137 |
| 6,305,578 B1 | 10/2001 | Hildebrandt et al. | | |
| 6,565,539 B1 * | 5/2003 | Zinger | ............. | A61B 17/00491 604/191 |
| 7,537,174 B2 * | 5/2009 | Redl | ................. | A61B 17/00491 222/137 |
| 7,635,343 B2 * | 12/2009 | McIntosh | .......... | A61B 17/00491 604/82 |
| 7,748,567 B2 * | 7/2010 | Horner | .................. | A61C 9/0026 222/135 |
| 8,096,449 B2 * | 1/2012 | Keller | .................. | B05C 17/0133 222/137 |
| 8,875,947 B2 * | 11/2014 | Obrist | .................. | B65D 81/325 222/137 |
| 8,985,394 B1 * | 3/2015 | Tapocik | ................ | A47K 5/1204 222/325 |
| 9,387,052 B2 * | 7/2016 | Muller | .................... | A61C 5/062 |
| 9,480,543 B2 * | 11/2016 | Keller | .................... | A61C 9/0026 |
| 2002/0146662 A1 * | 10/2002 | Radl | ......................... | A61C 5/64 433/90 |
| 2002/0160333 A1 | 10/2002 | Pierson et al. | | |
| 2004/0216591 A1 * | 11/2004 | Assadi | .............. | B05C 17/00513 89/1.14 |
| 2005/0243647 A1 | 11/2005 | Gray et al. | | |
| 2007/0012724 A1 * | 1/2007 | Feinberg | .......... | A61B 17/00491 222/137 |
| 2007/0164047 A1 * | 7/2007 | Reidt | .................... | A61C 9/0026 222/137 |
| 2007/0166660 A1 | 7/2007 | Peuker et al. | | |
| 2007/0175921 A1 * | 8/2007 | Keller | ................. | B05C 17/00506 222/137 |
| 2007/0228076 A1 * | 10/2007 | Horner | ................. | A61C 9/0026 222/135 |
| 2009/0060624 A1 * | 3/2009 | Schenck | .................. | A61C 5/62 401/171 |
| 2009/0142727 A1 | 6/2009 | Lawter et al. | | |
| 2009/0230214 A1 | 9/2009 | Keller | | |
| 2009/0302060 A1 | 12/2009 | Keller | | |
| 2010/0318063 A1 * | 12/2010 | Soll | ........................ | A61M 5/19 604/518 |
| 2011/0137262 A1 * | 6/2011 | Muller | .................... | A61C 5/062 604/222 |
| 2012/0189977 A1 * | 7/2012 | Vocke | ................. | B05C 17/00503 433/90 |

* cited by examiner

Section C-C

Fig. 7A

Section D-D

Fig. 7B

SYRINGE

CROSS-REFERENCE TO RELATED APPLICATIONS

This application is a National Stage application of International patent application PCT/EP2014/057167 filed on Apr. 9, 2014, which claims priority to German patent application No. 102013103552.3 filed on Apr. 9, 2013, the disclosures of which are incorporated herein by reference in their entirety.

The invention relates to a syringe for dispensing flowable dental materials according to the preamble of claim 1 and claim 17.

Syringes of this type have been known for a long time as syringes which were referred to as dual-chamber syringes. A dual-chamber syringe is known from CH 669 164 A1, for instance. In a syringe of this type two pistons for storage chambers are actuated collectively. In this way, the material stored in the storage chambers is squeezed out via the outlets of the storage chamber. Via mixing channels the material is supplied to a mixing device which has an outlet to which a cannula is attached.

For a long time dual-chamber syringes of this type have proven themselves in practice also for dental materials if different materials are to be combined shortly before the application thereof and to be applied together.

However, especially if dental materials are used, specific boundary conditions and aspects need to be taken into account in connection with the design of syringes of this type:

In many cases dental materials are of comparatively high quality such that it would be unfavorable if residues remained in the syringe which are not usable. This is why wake spaces are to be avoided, namely in the storage chambers and—and this is usually more difficult to achieve—in the dispensing and mixing areas.

On the other hand, in particular with dental materials, it is important to achieve a homogeneous and proper mixing of the materials. In case of incorrect mixing ratios completely different properties are imparted to the dental material, which may lead to adhesion problems. Also, if mixing has not been carried out sufficiently, corresponding degradations may occur.

In order to counteract this problem, suggestions have been made to realize a mixing device in the area of the cannula, for instance by purposefully mounting flow resistance devices, grids or the like.

On the other hand, flow resistance devices of this type increase the dispensing resistance and are considered unfavorable. In addition, the construction length of the syringe is increased, and this is considered unfavorable in terms of ergonomics. As an example hereof it is referred to U.S. Pat. No. 4,538,920 A1.

Thus, attempts have been made to provide other solutions for the application of substances which consist of two components, in particular in the dental field. As an example hereof it is referred to DE 101 24 819 A1.

In contrast, the invention is based on the task of providing a syringe, in particular for dispensing flowable dental materials, according to the preamble of claim 1 or claim 17, in which wake spaces in which unusable residues of materials are accumulated can be avoided if possible, and in which a smaller dispensing resistance can be combined with a proper mixing of the materials.

This task is inventively solved by claim 1 and by claim 17. Advantageous developments may be taken from the sub-claims.

According to the invention it is particularly favorable that, in spite of the use of relatively pasty but still flowable materials, fluidic measures have a positive effect on a proper mixing of materials when the flow resistance is low. Suprisingly, it has been found out that, in spite of the use of viscous materials, targeted flow deflections known per se ensure the proper mixing of materials when the flow resistance is relatively low.

The implementation of two impact zones is particularly advantageous in which different flows collide with each other. Surprisingly, as a result a better mixing of materials is achieved than when flow resistances are used, as is known from U.S. Pat. No. 4,538,920 A1, for instance.

According to the invention it is provided to provide the mixing device with a pre-mixing zone and a mixing zone for this purpose. In the pre-mixing zone a partial flow of the first material is supplied to another partial flow of a further material. The directions of flow on the inlet side of the pre-mixing zone, i.e. the directions of flow of the partial flows, point toward each other. In this connection, it is favorable if the directions of flow do not run in an antiparallel, but in a slightly inclined fashion, for instance at an angle of 150° to one another.

Likewise, a further partial flow of the first material is supplied to a further flow, i.e. to the fourth partial flow altogether, wherein the fourth partial flow consists of the second material. Here, too, the directions of flow of the partial flows point toward each other, but are preferably not antiparallel, but at an angle of approximately 150°. It is to be understood that the exact orientation can be adapted to the requirements to a large degree. An angle of 160°, of 140° or even of 130° or 120° is also possible.

The pre-mixed partial flows of both materials are then supplied from the pre-mixing zone to the mixing zone. In the pre-mixing zone a flow deflection around half the angle of the directions of flow of both partial flows is effected. Thus, in case of an angle of 150° the partial flows would be returned together at an acute angle of 75° and supplied to the mixing zone.

The pre-mixed partial flows flow to the mixing zone in an antiparallel fashion toward each other; here, too, a slight angular deviation from 180° is not undesired, for instance in the third dimension, too.

In the mixing zone at the latest the joining takes place by a collision of the partial mixing flows and by a deflection into the third dimension, i.e. substantially by 90°.

It has proven to be particularly favorable if the impact element comprises inclined or rounded or hollowed out surfaces. In this way, a flow resistance is provided which is as low as possible and the main mixing process takes place as a result of the collision of the partial flows which flow toward each other between the pre-mixing zone and the mixing zone and which are led together on the same path to the outlet of the mixing zone across the impact element.

The design of the outlet of the mixing zone is also of particularly favorable importance according to the invention. Preferably, the outlet is configured in the area of an additional deflection zone which comprises inclined surfaces which extend in consistency with the inclined surfaces of the impact element and which surround a baffle whose normal points toward the impact element.

In this way, a flow resistance is produced. However, this resistance is in the area of a flow expansion at which correspondingly smaller flow rates are obtained which leads to a correspondingly reduced flow resistance in terms of fluid mechanics. Surprisingly, this still results in particularly good post-mixing properties which are effected by means of the interaction of the impact element which is cone-shaped, for instance, with the counter inclined surfaces and the baffle of the deflection zone while the flow is expanded at the same time and subsequently constricted in the cannula channel.

The combination of the pre-mixing zone, the mixing zone and the deflection zone thus provides the particularly favorable mixing at low flow resistance according to the invention, wherein the condition for the provision of the pre-mixing zones is the separation of the base materials into different partial flows.

Thus, on the outlet side of every storage chamber two mixing channels are provided according to the invention which each diverge from each other and flow toward the respective opposite other mixing channel of the other material in an inclined manner. The pre-mixing zone arises as the result of the collision of respective partial flows which correspond to each other and comprises a curve on its side spaced apart from the mixing zone, said curve facilitating a low-resistance free flow of the partial flows in the mixing channels which point toward each other and in this way ensures the desired pre-vortexing process.

According to the invention, a pre-deflection of the partial mixing flows toward the mixing zone is consciously avoided in order not to endanger the inventively favorable pre-vortexing process.

According to the invention, it is particularly favorable if the mixing channels comprise a broad and flat cross section, for instance at a height/width ratio of 1:2.

In that case, all of the four mixing channels are preferably guided in one plane which runs perpendicularly to the dispensing direction of the syringe, i.e. to the axis of the cannula channel, whose plane normal is thus parallel to the axis of the cannula channel. Preferably, the pre-mixing zone and the mixing channels and also the inventive impact element are configured as respective indentations or elevations in an insert element whose mixing device side points toward the dispensing direction and correspondingly faces the cannula. In that case, only the deflection zone is configured in the cannula itself which in that case has a flat configuration pointing against the direction of discharge and which surrounds the deflection zone.

Figure 5:
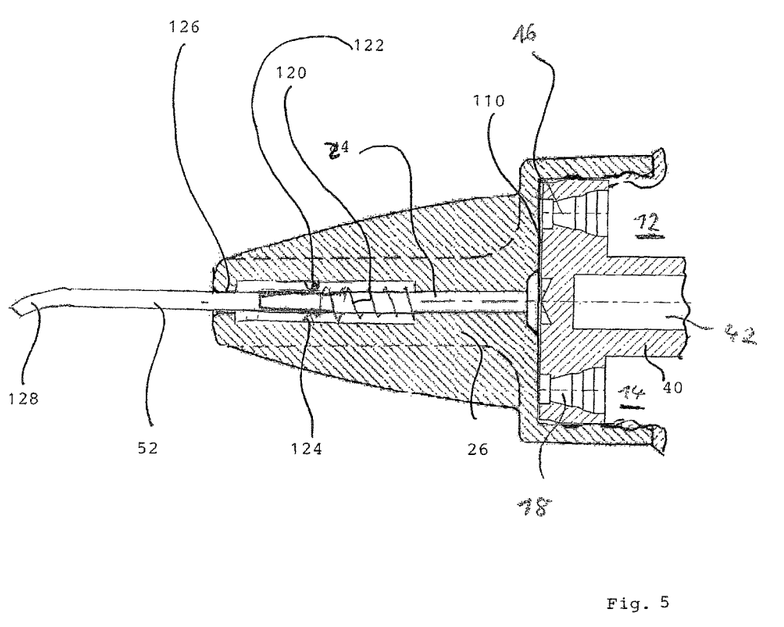
FIG. 5 shows a sectional view of a modified embodiment of the inventive syringe.

In an inventively advantageous embodiment, the ratio between the flow resistance and the mixing can be adjusted as desired by selecting the distance between the cannula and the insert element; a larger distance, as can be seen from FIG. 5, results in lower mixing and a lower flow resistance.

According to the invention it is particularly favorable if the mixture is realized by a predefined dosing device which reliably squeezes out a predefined amount of materials. When the material flows through the mixing device, at the start of the dispensing process and at the end of the dispensing process material is dispensed typically at a lower flow rate because the mass is initially accelerated upon start of the dosed dispensing process and decelerated towards the end.

According to the invention this dosing-related aspect does not have any negative effect on the mixing; the particles of both materials which are moving slowly through the pre-mixing zone are accelerated sufficiently upon arrival at the mixing zone such that the mixing process will finally take place sufficiently thereat.

Likewise, this applies to the deceleration process toward the end of the dosing process; intermixing will then already take place to a sufficient degree in the area of the pre-mixing zone such that the lower flow rate in the area of the mixing zone does not have any significant effect on the mixing process either.

In a particularly favorable embodiment it is provided that the storage chambers are formed as a cylinder with piston wherein the pistons can be actuated jointly by means of a piston drive, and that the piston drive comprises a dosing device which dispenses a respective predefined amount from the storage chambers upon actuation of an actuation element.

In addition, in a particularly favorable embodiment according to the invention the dosed output can also be shifted to the area of the cannula. In this case, mixing has already taken place—at a comparatively high flow rate—in the area of the mixing zone, the pre-mixing zone and the deflection zone, and in that case the dosed output is only effected for the base material which has already been intermixed by pressing a small cannula tube, a so-called pushing tip, against the spring force of a compression spring which pushes the small cannula tube towards the front out of the cannula channel against a stop.

In this connection, the selective actuation possibility for the application by means of an actuation element, for instance a button which can be pressed from the side, which acts on pistons of the storage chambers, and by means of the pushing tip, on the other hand, is particularly favorable.

In an advantageous embodiment it is provided that in the area of the pre-mixing zone the mixing device comprises a flow deflection which is configured in particular in an acute-angled manner.

In an advantageous embodiment it is provided that two pre-mixing zones—in terms of the mixing zone—are arranged opposite each other, and in that at least one mixing channel extends between each pre-mixing zone and each storage chamber outlet.

In an advantageous embodiment it is provided that storage chamber outlets comprise a circular cross-section and/or that the mixing channels comprise a rectangular cross section and/or that the impact element comprises a pyramid-shaped or cone-shaped or truncated cone-shaped or truncated pyramid-shaped cross section.

In an advantageous embodiment it is provided that at least two mixing channels extend from each outlet of a storage chamber, which mixing channels diverge from each other.

In an advantageous embodiment it is provided that the flow areas for the dental materials comprise a substantially constant cross-sectional area starting from the storage chamber to the mixing zone and that they are configured free from discontinuities such as wake spaces.

In an advantageous embodiment it is provided that each mixing channel comprises a length/diameter ratio of more than 2:1, in particular between 3:1 and 10:1, particularly preferable between 4:1 and 6:1, between the outlet and the pre-mixing zone, i.e. in the branched area.

In an advantageous embodiment it is provided that the deflection in the pre-mixing zone is effected in a plane relative to which the deflection in the mixing zone forms a third dimension.

In an advantageous embodiment it is provided that the directions of flow of the dental materials between the pre-mixing zones point toward each other and toward the mixing zone.

In an advantageous embodiment it is provided that to the outlet of the mixing zone a cannula is connected which comprises a cannula channel at whose front tip a small cannula tube is mounted, in particular rotatably.

In an advantageous embodiment it is provided that a small cannula tube is mounted in a slidably movable manner in a cannula downstream of a cannula channel which is attached to the outlet of the mixing zone, wherein the small cannula tube and the cannula channel have diameters which differ from each other by less than 30%, in particular by less than 10%.

In an advantageous embodiment it is provided that the small cannula tube is mounted in a slidably movable and spring loaded manner relative to the cannula channel, wherein the spring force points away from the mixing zone and the sliding movability of the small cannula tube relative to the cannula is limited by stops.

In an advantageous embodiment it is provided that the syringe comprises two drives for dispensing material which can be actuated simultaneously and independently of one another, that is to say for dispensing material by pressing a small cannula tube into a cannula and for dispensing material by actuating an actuation element which acts on a shared piston drive for the storage chambers.

In an advantageous embodiment it is provided that the outlet of the mixing zone comprises a deflection zone which extends between the cannula channel and the mixing zone and in that at said deflection zone inclined surfaces and baffles surround the inlet of the cannula channel and point toward the impact element.

In an advantageous embodiment it is provided that the deflection zone is configured as a truncated cone-shaped recess in the cannula which extends across the mixing zone and the impact element and has a larger flow area than the cannula channel.

In an advantageous embodiment it is provided that the normals of baffles which surround a cannula channel of the cannula extend parallel to the axis of the cannula channel.

In an advantageous embodiment it is provided that the mixing device has a mixing zone which is connected to a pre-mixing zone, and in that the mixing zone has an impact element for deflecting the pre-mixed flow of dental materials toward an outlet of the mixing zone, and in that a dosing device is configured such that it can be actuated by an actuation element for the shared piston drive of the pistons of the storage chamber independently of a pushing tip (small cannula tube) which is mounted in or to a cannula in a slidably movable manner, said cannula being connected to the outlet of the mixing zone.

Further advantages, details and features may be taken from the following description of several exemplary embodiments of the invention in conjunction with the drawing.

Figure 1:
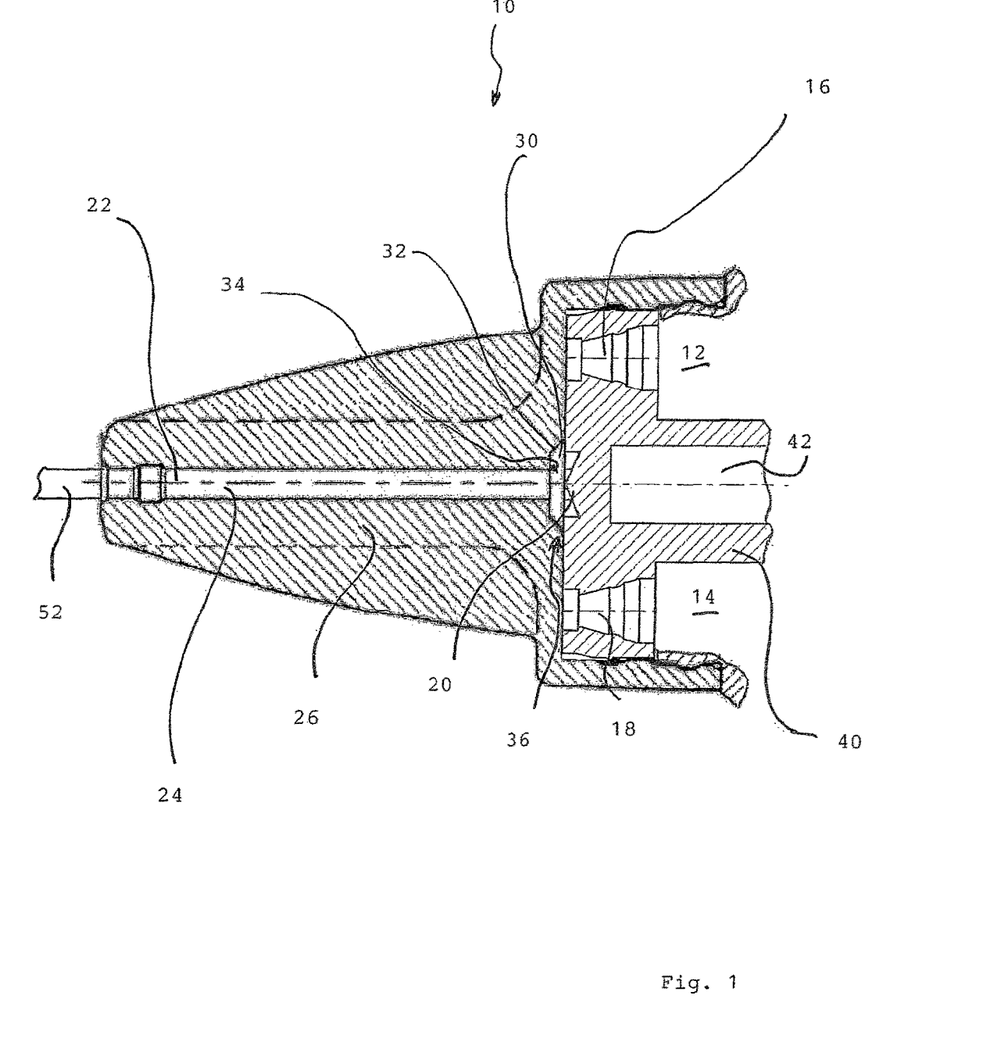
FIG. 1 shows a sectional view of a part of an inventive syringe by showing the parts which are important for the invention.

The syringe 10 illustrated in FIG. 1 comprises storage chambers 12 and 14 which are illustrated in a broken up view and which serve to receive dental materials. As dental materials of this type mixtures of the following material can be used:

Mixture of bis-acrylamide derivative, water, alcohol, bis-methacrylamide dihydrogen phosphate, acrylamide amino acid, highly dispersed silicon dioxide, initiators, catalysts and potassium fluoride.

It is to be understood that this list is not to be understood as an exhaustive list and that other materials can also be used.

On the outlet side of the storage chambers outlets 16 and 18 are provided which lead to mixing channels whose configuration is explained below based on FIG. 2.

Figure 2:
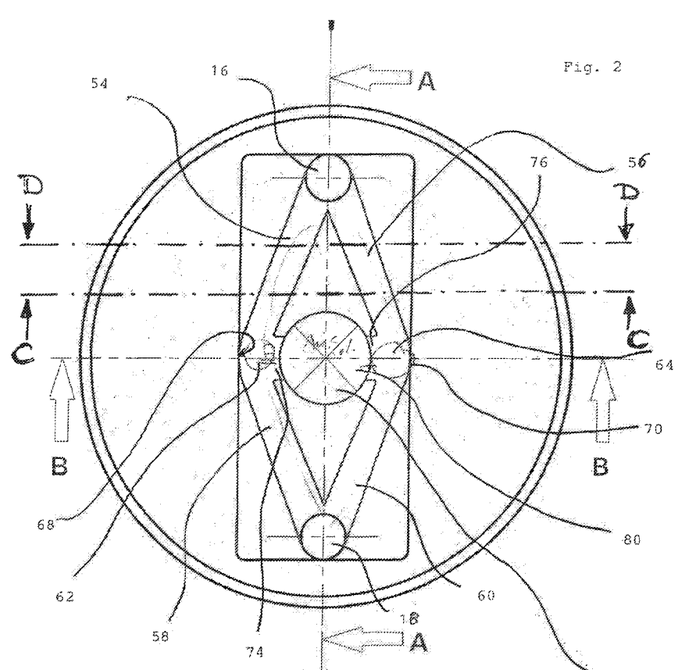
FIG. 2 shows a front view of an insert element in order to illustrate the embodiment according to FIG. 1 by showing the mixing channels, the pre-mixing zone and the mixing zone.

The mixing channels guide respective partial flows of materials from the storage chambers 12 and 14 toward each other and end in pre-mixing zones which can also be seen from FIG. 2. Starting from the pre-mixing zones, partial flows are supplied to the mixing zone. A part of the mixing zone is covered by an impact element 20 which can be seen in FIG. 1. In this way, the materials that have now been mixed are deflected into the dispensing direction of the syringe, that is to say in the direction of an axis 22 of a cannula channel 24 which is configured in a cannula 26.

On the inlet side of the cannula channel 24 a deflection zone 30 is configured which is opposite to the impact element 20. The deflection zone 30 comprises inclined surfaces 32 which surround the impact element 20 in their basic configuration and which are configured consensually with its inclined surfaces as well as baffles 34 which extend between the inclined surfaces 32 and the inlet of the cannula channel 24 and whose surface normal extends parallel to the axis 22.

The mixing channels, the pre-mixing zone, the mixing zone including the impact element 20 and the deflection zone 30 together form an inventive mixing device 36.

The cannula 26 is fitted or screwed onto the rest of the syringe 10 in a way known per se. In the exemplary embodiment illustrated, an insert element 40 pointing to the dispensing direction fits closely to its inside in which a major part of the mixing device 36 is configured.

The insert device 40 also comprises a guide recess 42 which receives a guide element for driving pistons of the storage chambers 12 and 14 jointly.

Upon actuation of a control button (not illustrated) which extends on the side of the syringe a drive element is actuated by means of push rods which extend to one another at an angle of 45° and which face toward each other, which drive element engages a gear rack and is used to move the pistons.

The front end 50 of the cannula channel 24 comprises a recess for receiving a small cannula tube 52. The small cannula tube can also be seen from FIG. 5 in an exemplary embodiment, and is preferably mounted rotatably in the cannula channel 24. In the embodiment according to FIG. 1 it is mounted rotatably in the cannula channel but not slidably in the direction of the axis 22, while it is mounted slidably in the embodiment according to FIG. 5. It is to be understood that the embodiments of FIGS. 1 and 5—as far as they differ from one another—can be combined with each other, respectively, which means that, for instance, a slidable mounting can also be provided in the embodiment according to FIG. 1.

FIG. 2 illustrates how the individual parts of the mixing device 36 can be realized in the insert element 40. Subsequent to the outlets 16 and 18 the mixing channels 54, 56, 58 and 60 extend, respectively. In this connection, the mixing channels 54 and 56 on the one hand and 58 and 60 on the other hand diverge from each other, respectively, for instance at an angle of between 20 and 70°, preferably at an angle of between 40 and 50°, for instance at an angle of 45°. They are symmetrical to one another such that all mixing channels 54 to 60 form a diamond shape, when considered jointly.

The mixing channels 54 to 60 each terminate in pre-mixing zones. In this connection, the mixing channels 54 and 58 terminate in the pre-mixing zone 62 and the mixing channels 56 and 60 in the pre-mixing zone 64. Each pre-mixing zone comprises fillets 68 and 70 toward the outside, respectively, that is to say at the side faces which are opposite to one another. The outlets 74 and 76 of the pre-mixing zones 62 and 64 point toward each other and lead to the mixing zone 80.

The mixing zone 80 comprises the impact element 20 as a central element. The impact element 20 is configured either in the style of a flat pyramid or as a cone, or possibly as a truncated cone. Alternatively, it can be configured in the shape of a segment of a sphere or paraboloid. Across the impact element 20 the partial flows from the outlets 74 and 76 of the pre-mixing zones 62 and 64 collide with each other and are correspondingly post-mixed in the mixing zone 80.

Figure 3:
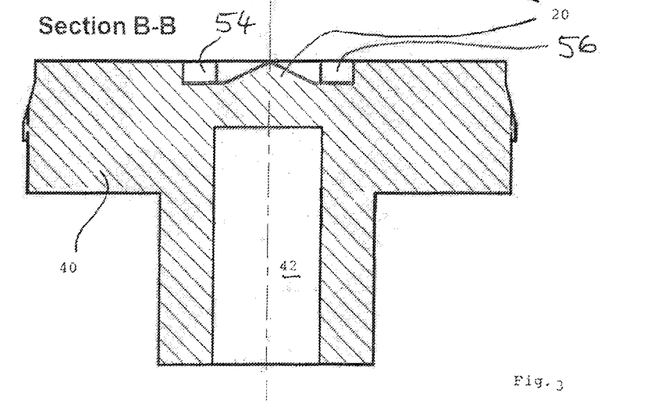
FIG. 3 shows a sectional view of the insert element by showing the impact element.

As can be seen from FIG. 3 the impact element 20 comprises a relatively large nose angle. Anyway, the nose angle is an obtuse angle and, for instance, amounts to between 110 and 160°, preferably to about 135°.

It can be seen that the impact element 20 is configured completely in the insert element 40.

Figure 4:
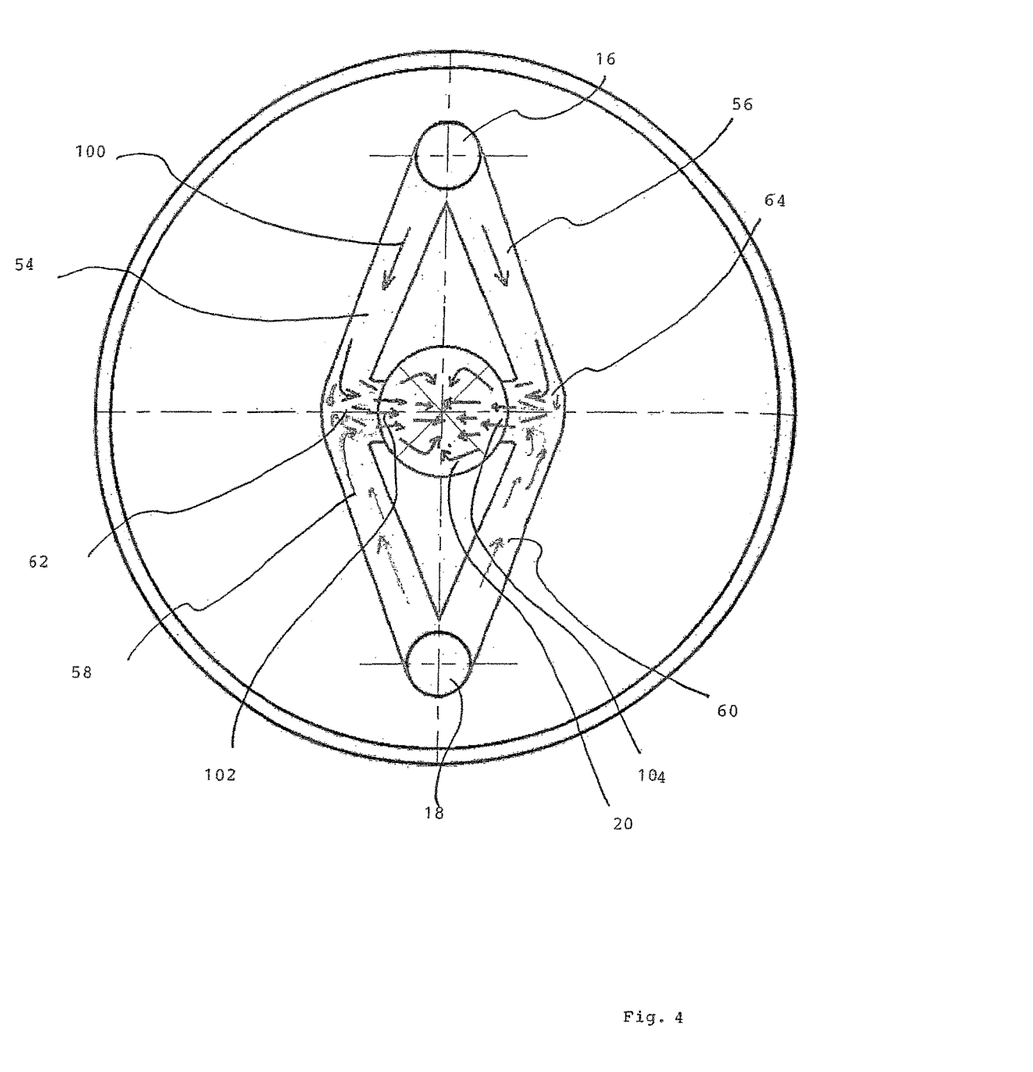
FIG. 4 shows a view of the partial flows of the mixing channels, the pre-mixing zone and the mixing zone according to the embodiment of FIG. 1.

It can be seen from FIG. 4 how the partial flows 100 in the mixing channels 54 to 60 diverge at first, starting from the outlets 16 and 18, and then collide with each other respectively in the pre-mixing zones 62 and 64 and are deflected thereat.

Above the impact element 20 there is a further collision of the partial flows 102 and 104 into the third dimension, that is to say out of the drawing plane in FIG. 4. This double deflection in two dimensions also leads to the materials being mixed well.

FIG. 5 shows a modified embodiment of the inventive syringe. In the rearward area of the cannula there is a gap 110 having a thickness of, for instance, 10 m between the cannula 26 and the insert element 40 which absorbs temperature-related movements of the individual parts of the syringe. Because of the shared entrance at the inlet of the cannula channel 24 the inventively intermixed material is squeezed out jointly.

In the front area of the cannula channel 24 the small cannula tube 52 is guided in a slidably movable and rotatably movable manner. For this purpose, the cannula channel 24 is configured as a tube which is inserted into the cannula 26. Then, the small cannula tube 52 is guided on this tube 24. A compression spring 120 which is biased between the cannula 26 and a rearward thickened portion 122 of the small cannula tube 52 is received such that it surrounds the front area of the cannula channel 24. The movement of the small cannula tube 52 toward the front is limited by a stop 124 which acts against the thickened portion 122. Furthermore, on the outlet side the small cannula tube 52 is guided by a relatively narrow through-recess 126 of the cannula 26 such that a good lateral stabilization is possible due to the guidance which is spaced apart.

As the small cannula tube can be rotated the syringe is particularly easy to handle even if it is actuated from the side, for instance, by means of a control button. In that case, the control button can remain at the same position, independent of whether the dentist treats the upper jaw or the lower jaw.

In an advantageous embodiment a cannula tube 24 is fixedly attached in the cannula 26, for instance by adhesive bonding, pressing and injection-molding or by welding. In this embodiment the cannula is pushed onto the small cannula tube 52 in a rotatable manner.

In a further modified embodiment the small cannula tube is configured of a flexible material which is preferably non-elastic and limp such that it remains at a certain position after it has been bent into a specific direction without resiling.

In the exemplary embodiment illustrated the small cannula tube 52 is provided with an offset 128 on the end side. It is to be understood that the offset can be configured in a more extreme or less extreme manner than illustrated in FIG. 5. If the offset is small, it is possible to squeeze out dental material similar to a pushing tip by head-on pressure to the small cannula tube 52. The dental material has already been mixed perfectly when it is in the small cannula tube 52 such that the low flow resistance which occurs at the start and the end of the insertion of the small cannula tube does not have any unfavorable effect on the mixing process.

Figure 6:
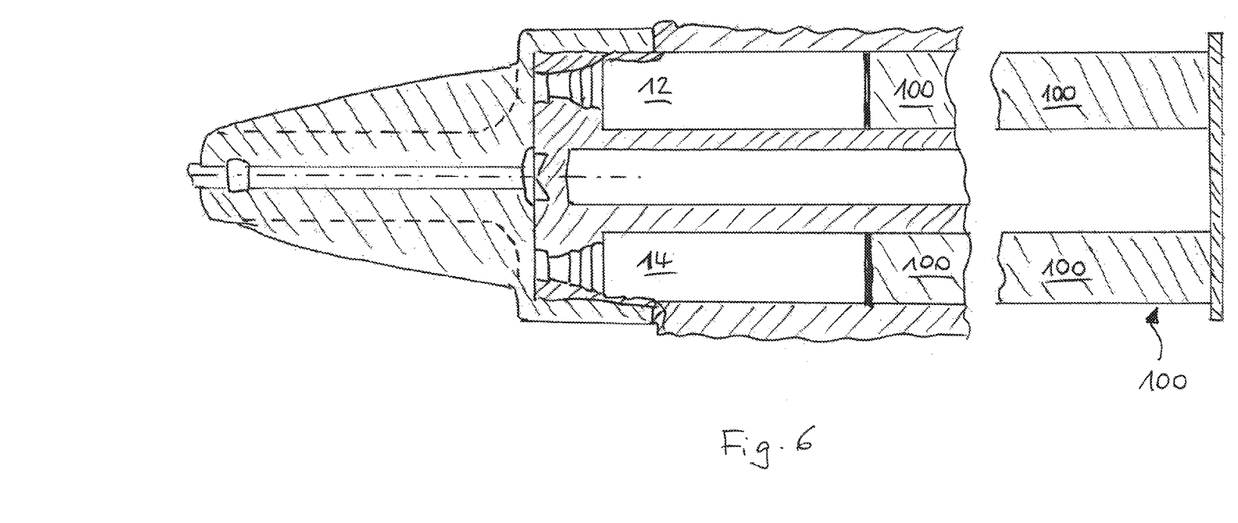
FIG. 6 shows a sectional view of a part of the inventive syringe.
Figure 7A:
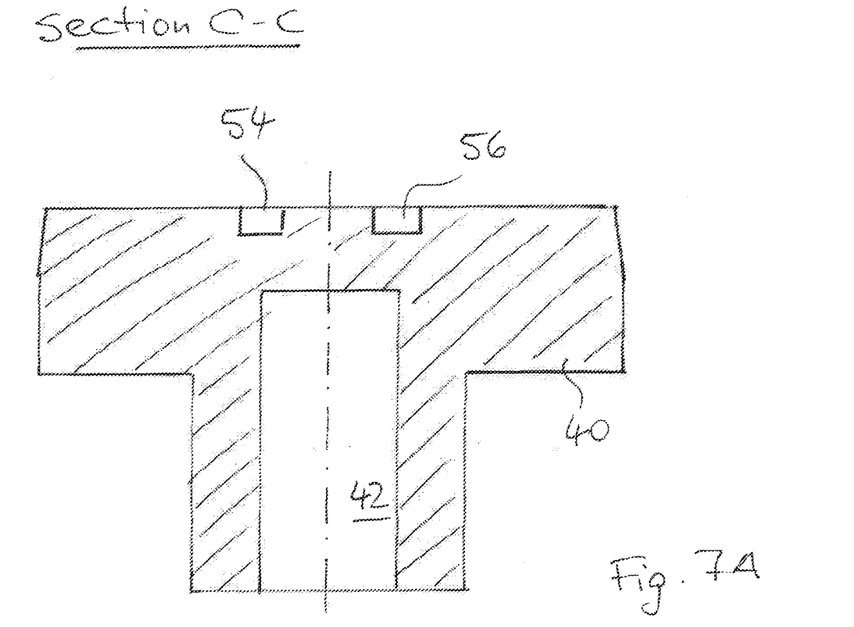
FIG. 7A shows a cross-sectional view taken at line C-C of FIG. 2.
Figure 7B:
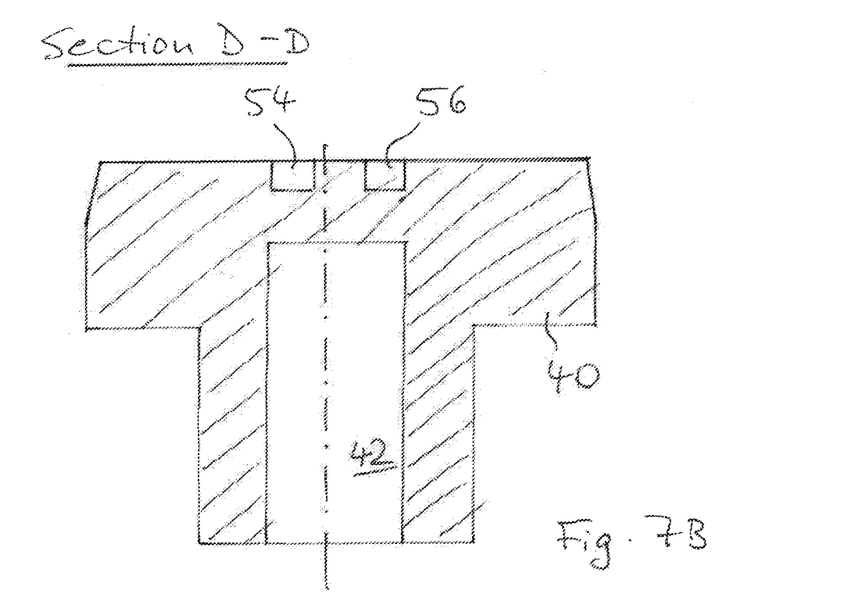
FIG. 7B shows a cross-sectional view taken at line D-D of FIG. 2.

In FIG. 6, dosing device 100 is shown in the storage chambers 12 and 14. FIG. 7A shows flow areas of the mixing channels 54 and 56 at line C-C of FIG. 2 FIG. 7B shows flow areas of the mixing channels 54 and 56 at line D-D of FIG. 2 These flow areas for the dental materials comprise a substantially constant cross-sectional area starting from the storage chamber (12 and 14) to the mixing zone (80) and are configured free from discontinuities and wake spaces.

The invention claimed is:

1. A syringe for dispensing flowable dental materials, comprising
   a syringe housing,
   at least two storage chambers (12 and 14) for dental materials, which lie transversely adjacent to each other as viewed in the dispensing direction, and
   a mixing device (36), which has at least two mixing channels (54, 56, 58, and 60), wherein each mixing channel is connected to an outlet of a storage chamber (12 and 14),
   characterized in that the mixing device (36) has a mixing zone (80), which is connected to a pre-mixing zone (64) and in that the pre-mixing zone (64) has two inlets, one for each of the dental materials to be mixed, and an outlet, wherein the inlets point toward each other and the outlet of the pre-mixing zone (64) extends perpendicularly to the inlets, and in that an inlet of the mixing zone (80) is connected to the outlet of the pre-mixing zone (64) and in that the mixing zone (80) has an impact element which is configured to deflect the pre-mixed flow of the dental materials to an outlet of the mixing zone (80), and in that a deflection zone is disposed between the impact element and a cannula channel.

2. The syringe as claimed in claim 1, characterized in that in the pre-mixing zone (64) the mixing device (36) comprises a flow deflection which is configured in an acute-angled manner.

3. The syringe as claimed in claim 2, characterized in that the deflection in the pre-mixing zone (64) is effected in a plane relative to which the deflection in the mixing zone (80) forms a third dimension.

4. The syringe as claimed in claim 1, characterized in that the pre-mixing zone comprises two pre-mixing zones (64) that are arranged opposite each other, and in that at least one of the at least two mixing channels extends between each of the two pre-mixing zone (64) and each storage chamber outlet.

5. The syringe as claimed in claim 1, characterized in that storage chamber outlets comprise a circular cross section and/or that the at least two mixing channels (54, 56, 58, and 60) comprise a rectangular cross section and/or that the impact element (20) comprises a pyramid-shaped or cone-shaped or truncated cone-shaped or truncated pyramid-shaped cross section.

6. The syringe as claimed in claim 1, characterized in that the at least two mixing channels (54, 56, 58, and 60) extend from each outlet of the storage chamber (12 and 14), which at least two mixing channels diverge from each other.

7. The syringe as claimed in claim 1, characterized in that flow areas for the dental materials comprise a constant cross-sectional area starting from the storage chamber (12 and 14) to the mixing zone (80) and that the flow areas are configured free from discontinuities and wake spaces.

8. The syringe as claimed in claim 1, characterized in that each mixing channel comprises a length/diameter ratio of more than 2:1 between the outlet and the pre-mixing zone (64), in a branched area.

9. The syringe as claimed in claim 8, characterized in that the length/diameter ratio is between 3:1 and 10:1, between the outlet and the pre-mixing zone (64), in the branched area.

10. The syringe as claimed in claim 8, characterized in that the length/diameter ratio is between 4:1 and 6:1, between the outlet and the pre-mixing zone (64), in the branched area.

11. The syringe as claimed in claim 1, characterized in that the pre-mixing zone comprises two pre-mixing zones (64) and directions of flow of the dental materials between the two pre-mixing zones (64) point toward each other and toward the mixing zone (80).

12. The syringe as claimed in claim 1, characterized in that to the outlet of the mixing zone (80) a cannula (26) is connected which comprises a cannula channel (24) having a front tip with a small cannula tube (52) mounted thereon.

13. The syringe as claimed in claim 12, wherein the small cannula tube (52) is rotatable.

14. The syringe as claimed in claim 1, characterized in that a small cannula tube (52) is mounted in a slidably movable manner in a cannula (26) down-stream of a cannula channel (24) which is attached to the outlet of the mixing zone (80), wherein the small cannula tube (52) and the cannula channel (24) have diameters which differ from each other by less than 30%.

15. The syringe as claimed in claim 14, characterized in that the small cannula tube (52) is mounted in a slidably movable and spring loaded manner relative to the cannula channel (24), wherein the spring force points away from the mixing zone (80) and the sliding movability of the small cannula tube (52) relative to the cannula (26) is limited by stops.

16. The syringe as claimed in claim 14, wherein the small cannula tube (52) and the cannula channel (24) have diameters which differ from each other by less than 10%.

17. The syringe as claimed in claim 1, characterized in that the syringe (10) comprises two drives for dispensing material which can be actuated simultaneously and independently of one another, for dispensing material by pressing a small cannula tube (52) into a cannula (26) and for dispensing material by actuating an actuation element which acts on a shared piston drive for the storage chambers (12 and 14).

18. The syringe as claimed in claim 1, characterized in that at said deflection zone (30) inclined surfaces and baffles surround an inlet of the cannula channel (24) and point toward the impact element (20).

19. The syringe as claimed in claim 18, characterized in that the deflection zone (30) is configured as a truncated cone-shaped recess in a cannula (26) which extends across the mixing zone (80) and the impact element (20) and has a larger flow area than the cannula channel (24).

20. The syringe as claimed in claim 18, characterized in that normals of baffles which surround a cannula channel (24) of a cannula (26) extend parallel to the axis (22) of the cannula channel (24).

21. A syringe for dispensing flowable dental materials, comprising
a syringe housing,
at least two storage chambers (12 and 14) for the dental material, which lie transversely adjacent to each other as viewed in the dispensing direction, and
a mixing device (36), which has at least two mixing channels (54, 56, 58, and 60), wherein each mixing channel is connected to the outlet of the storage chamber (12 and 14),
characterized in that the mixing device (36) has a mixing zone (80) which is connected to a pre-mixing zone (64), and in that the mixing zone (80) has an impact element (20) for deflecting which is configured to deflect the pre-mixed flow of dental materials toward an outlet of the mixing zone (80), and in that a dosing device is configured such that it can be actuated by an actuation element for the shared piston drive of the pistons of the storage chamber independently of a pushing tip comprising a small cannula tube (52) which is mounted in or to a cannula (26) in a slidably movable manner, said cannula being connected to the outlet of the mixing zone (80), and in that a deflection zone is disposed between the impact element and a cannula channel.

* * * * *